(12) United States Patent
Sanpitak

(10) Patent No.: US 11,246,545 B2
(45) Date of Patent: Feb. 15, 2022

(54) PATIENT BED ELECTRONIC RULER

(71) Applicant: Siemens Medical Solutions USA, Inc., Malvern, PA (US)

(72) Inventor: Patanit Sanpitak, Highland Park, IL (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 204 days.

(21) Appl. No.: 16/644,182

(22) PCT Filed: Oct. 20, 2017

(86) PCT No.: PCT/US2017/057593
§ 371 (c)(1),
(2) Date: Mar. 4, 2020

(87) PCT Pub. No.: WO2019/078884
PCT Pub. Date: Apr. 25, 2019

(65) Prior Publication Data
US 2020/0375553 A1 Dec. 3, 2020

(51) Int. Cl.
A61B 6/00 (2006.01)
A61B 6/04 (2006.01)
(Continued)

(52) U.S. Cl.
CPC .......... A61B 6/0492 (2013.01); A61B 6/0407 (2013.01); A61B 6/467 (2013.01);
(Continued)

(58) Field of Classification Search
CPC .. A61B 2090/061; A61B 6/0407; A61G 7/05; A61G 7/00; G01B 11/02; G01B 11/14; G01B 17/00
See application file for complete search history.

(56) References Cited

U.S. PATENT DOCUMENTS

2005/0110976 A1   5/2005   Labelle
2007/0261255 A1  11/2007   Cooper et al.
2009/0033917 A1*  2/2009   Bak .................. A61B 6/037
                                                356/73

FOREIGN PATENT DOCUMENTS

JP   H01189509 A   7/1989
JP   2006078369 A  3/2006
(Continued)

OTHER PUBLICATIONS

International Search Report for corresponding application No. PCT/IUS2017/057593 dated Jul. 13, 2018.

Primary Examiner — Dani Fox

(57) ABSTRACT

Embodiments can provide a medical imaging patient bed with an integrated electronic ruler system, comprising a light strip, mounted to the medical imaging bed; a trough comprising an open end and a closed end, mounted to the medical imaging bed and oriented such that the light strip is bounded by the open end and the closed end of the trough; a laser distance meter attached to the open end of the trough; a microcontroller; and a power source configured to provide power to the light strip, laser distance meter, and microcontroller; wherein the microcontroller is configured to illuminate the light strip after one or more distance measurements are received from the laser distance meter when an object is inserted into the trough; wherein a position of the illumination of the light strip corresponds to the one or more distance measurements received from the laser distance meter.

24 Claims, 3 Drawing Sheets

(51) Int. Cl.
*G01B 11/14* (2006.01)
*G01B 17/00* (2006.01)
*A61B 90/00* (2016.01)

(52) U.S. Cl.
CPC .............. *A61B 6/545* (2013.01); *A61B 6/547* (2013.01); *A61B 6/582* (2013.01); *G01B 11/14* (2013.01); *G01B 17/00* (2013.01); *A61B 2090/061* (2016.02)

(56) References Cited

FOREIGN PATENT DOCUMENTS

| | | |
|---|---|---|
| JP | 2012030042 A | 2/2012 |
| JP | 2017010383 A | 1/2017 |
| WO | 2007066638 A1 | 6/2007 |
| WO | 2016125904 A1 | 2/2016 |

* cited by examiner

PATIENT BED ELECTRONIC RULER

TECHNOLOGY FIELD

The present device relates to a system allowing for a care provider or other user to easily mark distances on a patient bed.

BACKGROUND

Current imaging patient beds lack the ability for a user to easily mark scan limits in reference to the patient body position on the scanning bed (especially in the case of whole body imaging). Previous solutions have included adhering a physical ruler to the patient bed, which required a user to manually enter the scan limits. Other solutions included the use of an array of linear encoding electromechanical switches along the patient bed that marked the scan limits electronically. However, this method was cumbersome to use and the materials were relatively expensive.

SUMMARY

Embodiments can provide a medical imaging patient bed with an integrated electronic ruler system, comprising a light strip, mounted to the medical imaging bed; a trough comprising an open end and a closed end, mounted to the medical imaging bed and oriented such that the light strip is bounded by the open end and the closed end of the trough; a laser distance meter attached to the open end of the trough; a microcontroller; and a power source configured to provide power to the light strip, laser distance meter, and microcontroller; wherein the microcontroller is configured to illuminate the light strip after one or more distance measurements are received from the laser distance meter when an object is inserted into the trough; wherein a position of the illumination of the light strip corresponds to the one or more distance measurements received from the laser distance meter.

Embodiments can further provide a medical imaging patient bed wherein the light strip further comprises one or more lights, the one or more lights configured to illuminate based on one or more commands sent from the microcontroller.

Embodiments can further provide a medical imaging patient bed wherein the microcontroller is further configured to illuminate a plurality of the one or more lights corresponding to a range of distance measurements received from the laser distance meter.

Embodiments can further provide a medical imaging patient bed wherein the laser distance meter further comprises a laser source configured to emit an emitted laser; and a laser receiver configured to receive a reflected laser; wherein the time between the emission of the emitted laser and the reception of the reflected laser determines the distance measurement.

Embodiments can further provide a medical imaging patient bed wherein the laser distance meter further comprises a laser source configured to emit an emitted laser; and a laser receiver configured to receive a reflected laser; wherein the triangulation of the emitted laser and the reflected laser determines the distance measurement.

Embodiments can further provide a medical imaging patient bed wherein the trough and the light strip each have a length substantially similar to the length of the medical imaging patient bed.

Embodiments can further provide a medical imaging patient bed wherein the microcontroller is further configured to communicate the one or more distance measurements to an imaging system host controller.

Embodiments can further provide a medical imaging patient bed wherein the imaging system host controller is configured to adjust one or more parameters of a medical imaging scan based upon the one or more distance measurements received from the microcontroller.

Embodiments can further provide a medical imaging patient bed wherein the imaging system host controller is configured to use the one or more distance measurements for at least one of: creating one or more virtual switches, detecting one or more swipe gestures, adjusting one or more ranges, and detecting one or more imaging scan limits.

Embodiments can further provide a medical imaging patient bed wherein the microcontroller is further configured to extinguish the light strip and reset the laser distance meter after receiving a reset command.

Embodiments can further provide a medical imaging patient bed with the closed end of the trough further comprising a reflective portion; wherein the distance meter is configured to be calibrated based on a distance measurement taken from the reflective portion of the trough.

Embodiments can further provide an electronic ruler system, comprising a light strip; a trough comprising an open end and a closed end; a distance meter attached to the open end of the trough; and a microcontroller; wherein the light strip is oriented such that the light strip is bounded by the open end and the closed end of the trough; wherein the microcontroller is configured to illuminate the light strip after one or more distance measurements are received from the distance meter when an object is inserted into the trough; wherein a position of the illumination of the light strip corresponds to the one or more distance measurements received from the distance meter.

Embodiments can further provide an electronic ruler system wherein the light strip further comprises one or more lights, the one or more lights configured to illuminate based on one or more commands sent from the microcontroller.

Embodiments can further provide an electronic ruler system wherein the microcontroller is further configured to illuminate a plurality of the one or more lights corresponding to a range of distance measurements received from the distance meter.

Embodiments can further provide an electronic ruler system wherein the distance meter comprises at least one of a laser distance meter, an ultrasound distance meter, or an infrared distance meter.

Embodiments can further provide an electronic ruler system wherein the at least one of the laser distance meter, ultrasound distance meter, or the infrared distance meter determines the one or more distance measurements through a time-of-flight determination.

Embodiments can further provide an electronic ruler system wherein the laser distance meter determines the one or more distance measurements through an optical triangulation.

Embodiments can further provide an electronic ruler system wherein the trough and the light strip are attached to a patient bed; the trough and the light strip each having a length substantially similar to the length of the patient bed.

Embodiments can further provide an electronic ruler system wherein the microcontroller is further configured to communicate the one or more distance measurements to a host controller.

Embodiments can further provide an electronic ruler system wherein the host controller is configured to use the one or more distance measurements for at least one of:

creating one or more virtual switches, detecting one or more swipe gestures, adjusting one or more ranges, and detecting one or more imaging scan limits.

Embodiments can further provide an electronic ruler system wherein the microcontroller is further configured to extinguish the light strip and reset the distance meter after receiving a reset command.

Embodiments can further provide an electronic ruler system with the closed end of the trough further comprising a reflective portion; wherein the distance meter is configured to be calibrated based on a distance measurement taken from the reflective portion of the trough.

Embodiments can further provide a method of using an electronic ruler system, comprising generating, by a laser distance meter, an emitted laser; receiving, by the laser distance meter, a reflected laser caused by the reflection of the emitted laser onto an object; generating, by the laser distance meter, based upon properties of the emitted laser and the reflected laser, one or more distance measurements; communicating, to a microcontroller, the one or more distance measurements; and illuminating, by the microcontroller, a light strip in a manner corresponding to the one or more distance measurements received from the laser distance meter.

Embodiments can further provide a method further comprising communicating, by the microcontroller, the one or more distance measurements to a host controller; and adjusting, by the host controller, one or more parameters of a medical imaging session based upon the one or more distance measurements.

BRIEF DESCRIPTION OF THE DRAWING FIGURES

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures.

DETAILED DESCRIPTION

Embodiments of the present invention involve a system and method for providing bedside measurements during imaging and other medical sequences in a non-invasive manner using a laser, ultrasound, or infrared rangefinder, one or more LEDs, and a microcontroller connected to a host controller. In embodiments, the electronic ruler can display measurements graphically, or provide a digital output directly integrated into one or more medical systems.

Figure 1:
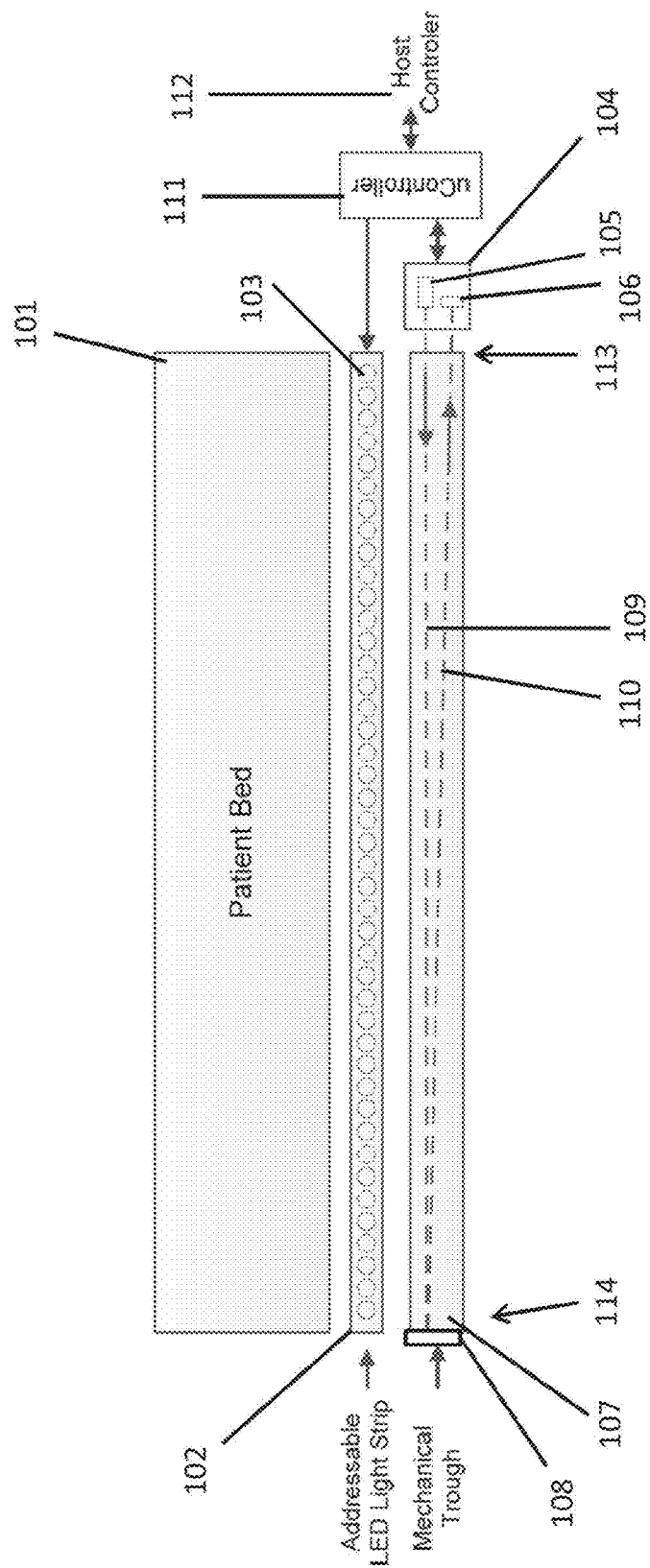
FIG. 1 illustrates a graphical representation of the electronic ruler system, in accordance with embodiments described herein.

FIG. 1 illustrates a graphical representation of the electronic ruler system, in accordance with embodiments described herein. The electronic ruler system can be directly attached to a patient bed 101, or can be modular and detachable such that the system can be moved from bed to bed if needed. The electronic ruler system can have a light strip 102, which can be comprised of one or more lights 103. In an embodiment, the one or more lights 103 can be LEDs, but any high-efficiency lighting solutions can be contemplated. The one or more lights 103 can be the same or different colors, or can be color-changing LEDs. Alternatively, the light strip can comprise a single, long screen comprising one or more pixels, which can function in a similar manner to the one or more lights. In an embodiment, the light strip 102 can be positioned behind a wire mesh or other protective screen. In an embodiment, the light strip 102 can be mounted to the trough 107, or can be a separate unit attached to the patient bed 101. The resolution of the light strip 102 can vary based on the number of lights 103 incorporated into the light strip 102: more lights 103 will translate into a finer resolution.

To sense distances, the electronic ruler system can use a laser distance meter 104, which can comprise a laser source 105 and a laser receiver 106. The laser distance meter 104 can be configured to produce emitted laser light 109 from the laser source 105, which can travel within a trough 107. The trough can have an open end 113, to which the laser distance meter 104 can be attached, and a reflective portion 108 located at a closed end 114. The trough 107 can be made of, among other things, metal, plastics, or composites thereof. In an embodiment, the trough 107 can be the same length as the patient bed 101. The trough 107 can be mounted on the side of the patient bed 101 at a waist-level height, such as on the top of the frame around the height of the bottom of the mattress. In an embodiment, the light strip 102 can be mounted on the frame of the patient bed 101 directly above the trough 107. In an embodiment, the light strip 102 can be mounted to the trough 107 in an L shape, or can be mounted separately from the trough 107. At the end of the trough 107 opposite the laser distance meter 104, an end reflective portion 108, which can be a mirror or other reflective surface, can reflect the emitted laser light 109 and produce reflected laser light 110, which can travel back along the trough 107 and be detected by the laser receiver 106. Use of the reflective portion 108 can aid calibration and resetting the laser distance meter 104 after use by a user.

In an embodiment, a visual laser source 105, such as a red laser can be used. Alternatively, an infrared laser or other low power laser can be used by the laser distance meter 104. In an alternative embodiment, an ultrasound distance meter or an infrared (but non-laser) distance meter can be used in place of the laser distance meter 104, and can use an ultrasound source and ultrasound receiver or an infrared source and infrared receiver, respectively, to measure distances.

The electronic ruler can control the light strip 102 and the laser distance meter 104 through the use of a microcontroller 111, which can moderate the interactions between the laser distance meter 104 and the light strip 102. The microcontroller 111 can interface with a host controller 112, which can be tied to a particular medical system, such as an imaging system. In this way, the microcontroller 111, in addition to visually displaying the measured distance through the light strip 102, can also send a digital value of the measured signal to the host controller 112 for display or recordation on the particular system being used.

Figure 2:
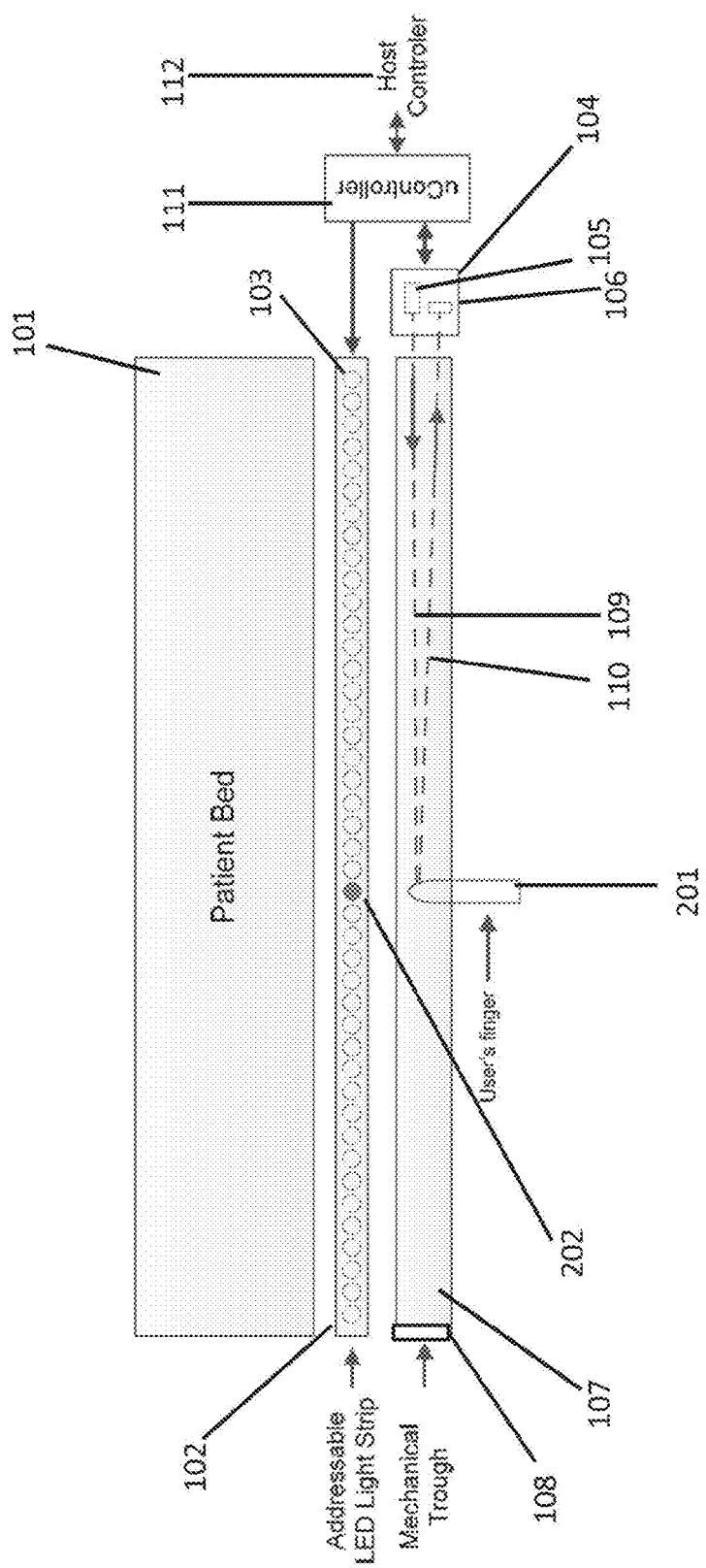
FIG. 2 illustrates a method of using the electronic ruler system, in accordance with embodiments described herein.

FIG. 2 illustrates a method of using the electronic ruler system, in accordance with embodiments described herein. As described above, the laser distance meter 104 can continuously produce, through the laser source 105, an emitted laser beam 109. Without obstruction, the emitted laser beam 109 can move along the trough 107, be reflected off of the reflective portion 108 of the trough 107, and return as a reflected laser beam 110 to the laser receiver 106. To use the electronic ruler system to make a measurement, a user can insert a finger 201 (or other object) into the trough 107 at a desired distance. The desired distance can correspond to an area just imaged, the location of a body part, or another metric determined to be important to the user. By inserting a finger 201 into the trough, the emitted laser light 109 is truncated, and the reflected laser light 110 returns with a different time than when unobstructed. This is also known as a time-of-flight calculation. The reflected laser light 110 is received by the laser receiver 106, and a distance value can be communicated to the microcontroller 111. Based on the distance value sent to the microcontroller 111, the microcontroller 111 can send a command to the light strip 102 to activate one or more lights 103. The illuminated light 202 can correspond in position to the user's finger 201 in the trough 107.

Alternately, the emitted laser beam 109 and reflected laser light 110 can be used to determine distance through optical triangulation instead of time-of-flight. In optical triangulation, the distance of the object 201 can be calculated through a measurement of the angular difference between the emitted laser beam 109 and the reflected laser light 110, which can vary based upon the object's 201 distance from the laser source 105 and the laser receiver 106.

In an embodiment, a single light 103 can be illuminated. In an alternate embodiment, the microcontroller 111 can illuminate one or more lights, including all of the lights between the user's finger and the end of the light strip 103 closest to the laser distance meter 104, or a pattern of lights where some are illuminated and some are extinguished. In an embodiment, the lights can remain constantly illuminated, or can illuminate and extinguish in a periodic fashion. In an embodiment, the illuminated light 202 can remain illuminated for as long as the user's finger 201 remains at the corresponding distance, and can extinguish when the user's finger 201 is removed. Alternatively, the illuminated light 202 can remain on for a predetermined interval after the user's finger 201 is removed, or can remain illuminated until a reset is communicated by the microcontroller 111. If the user elects to move the finger 201 within the trough 107, the lights 103 can be illuminated or extinguished as needed to follow the distance path of the user's finger. In an embodiment, the user can designate one or more measurements by placing and removing the finger 201 at differing distances, leading to the illumination of multiple lights 103 that correspond to those distances. The light strip 102 can completely extinguish when a reset command is sent by the microcontroller 111, or when the user makes a particular swipe gesture preconfigured to clear the light strip.

As described above, as the one or more lights 103 are illuminated, a digital value of the distance measured can be communicated by the microcontroller 111 to a host controller 112 for storage, use, and/or display on a screen or monitor. In an embodiment, each time a user's finger 201 is inserted into the trough 107, a measurement communication can occur between the microcontroller 111 and the host controller 112. Depending on the particular user interface used with the electronic ruler system, the microcontroller 111 can also direct the user interface to mark the distance (for instance, by imposing scan limits for a medical imaging scan), display a distance range (for instance, a scan range), clear the distance measurement, or report the positions to the host controller 112.

Figure 3:
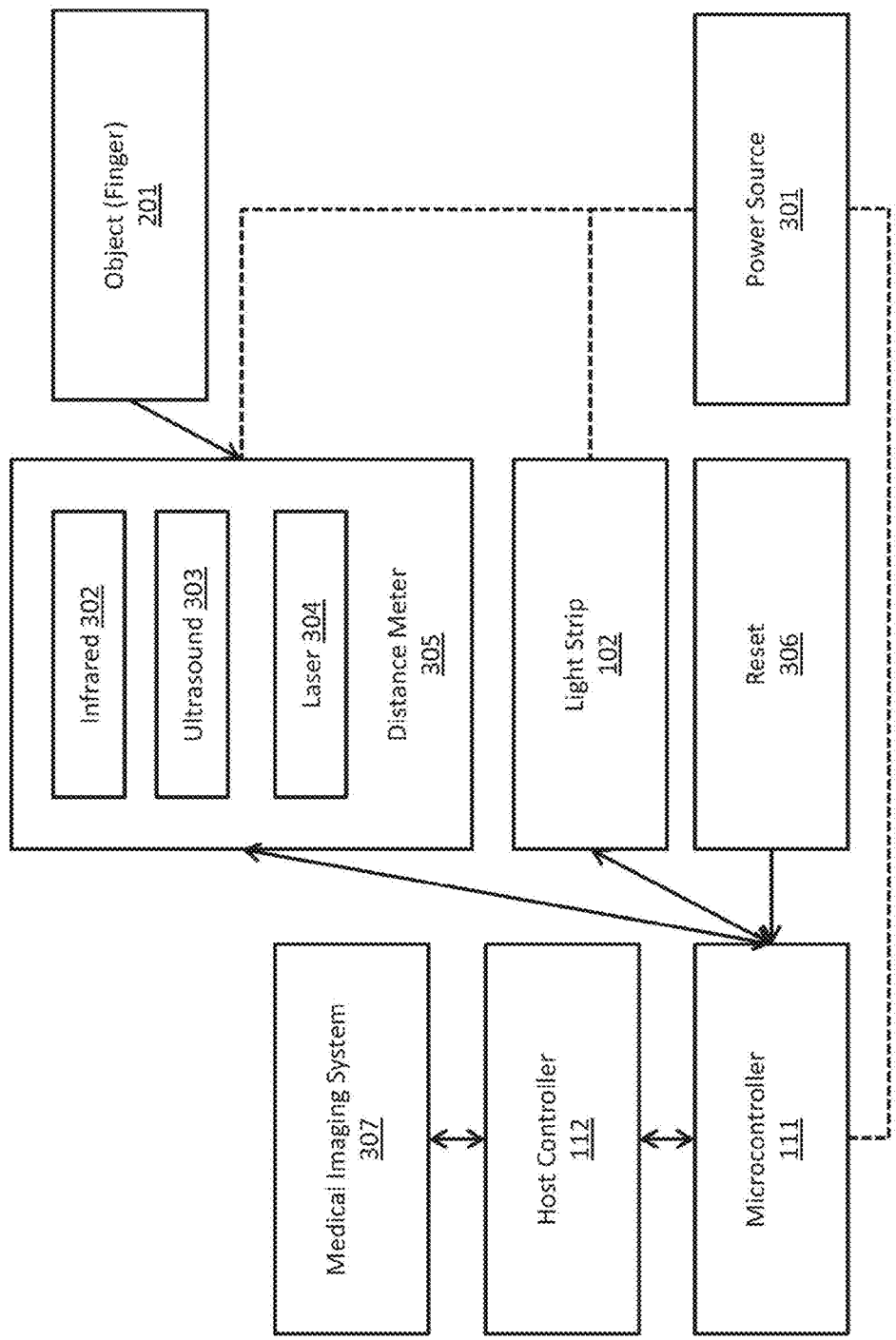
FIG. 3 depicts a block diagram illustrating various components of the electronic ruler, in accordance with embodiments described herein.

FIG. 3 depicts a block diagram illustrating various components of the electronic ruler, in accordance with embodiments described herein. As discussed above, the electronic ruler system can be controlled via a microcontroller 111, which can mediate the interactions between a distance meter 305 and a light strip 102. As the object (i.e., the user's finger) 201 interacts with the distance meter 305 within the trough, the microcontroller 111 can turn lights in the light strip 102 on and off as they correspond with the distances measured. If one or more lights are illuminated (for instance, in visually displaying a scan range), the system can be completely returned to basic operating state through the use of a reset command 306, which can be sent via a switch, button, toggle, or software command. Basic operating state can include extinguishing the light strip 102 and resetting the distance meter 305. Additionally, the measured distances can be output by the microcontroller 111 to the host controller 112, which in turn can communicate with a medical imaging system 307. The electronic ruler system can be powered by a power source 301, which can be an external plug or a battery. A battery can be used for portability, such that a patient bed with the electronic ruler installed can be moved between rooms or within a large room without the need to unplug and replug in the system.

Modes of measurement by the distance meter 305 can include a laser distance meter 304, an ultrasonic distance meter 303, or an infrared distance meter 302. In an embodiment, the laser distance meter 304, ultrasonic distance meter 303, and infrared distance meter 302 can determine distance through time-of-flight. Alternatively, the laser distance meter 304 can determine distance through optical triangulation.

Other uses of the electronic ruler system can include detecting and marking imaging scan limits (or scan ranges), adjusting scan ranges from either end of the scan limits, moving the scan range, creating 'virtual switches' for user to select preset range mode or other modes of operations, or detecting user 'swipe gestures' as another means of user input control. Each of these functions can be activated or accomplished through the use of pre-programmed gesture commands. In an embodiment, a set of commands can be selected based on the use of the electronic ruler (for instance, one set for medical imaging, another set for general patient measurements).

Advantages of the system include higher reliability (due to the lack of electromechanical switches), a continuous feel and response for a user as compared to a discrete array of electromechanical switches, ease of compliance with IEC-60601-1, Safety, and EMC, and flexibility of user input control and user display feedback.

The present description and claims may make use of the terms "a," "at least one of," and "one or more of," with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples are intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the example provided herein without departing from the spirit and scope of the present invention.

The system and processes of the figures are not exclusive. Other systems, processes, and menus may be derived in accordance with the principles of embodiments described herein to accomplish the same objectives. It is to be understood that the embodiments and variations shown and described herein are for illustration purposes only. Modifications to the current design may be implemented by those skilled in the art, without departing from the scope of the embodiments. As described herein, the various systems, subsystems, agents, managers, and processes can be implemented using hardware components, software components, and/or combinations thereof. No claim element herein is to be construed under the provisions of 35 U.S.C. 112, sixth paragraph, unless the element is expressly recited using the phrase "means for."

Although the invention has been described with reference to exemplary embodiments, it is not limited thereto. Those skilled in the art will appreciate that numerous changes and modifications may be made to the preferred embodiments of the invention and that such changes and modifications may be made without departing from the true spirit of the invention. It is therefore intended that the appended claims be construed to cover all such equivalent variations as fall within the true spirit and scope of the invention.

I claim:

1. A medical imaging patient bed with an integrated electronic ruler system, comprising:
    a light strip, mounted to the medical imaging bed;
    a trough comprising an open end and a closed end, mounted to the medical imaging bed and oriented such that the light strip is bounded by the open end and the closed end of the trough;
    a laser distance meter attached to the open end of the trough;
    a microcontroller; and
    a power source configured to provide power to the light strip, laser distance meter, and microcontroller;
    wherein the microcontroller is configured to illuminate the light strip after one or more distance measurements are received from the laser distance meter when an object is inserted into the trough;
    wherein a position of the illumination of the light strip corresponds to the one or more distance measurements received from the laser distance meter.

2. The medical imaging patient bed as recited in claim 1, wherein the light strip further comprises one or more lights, the one or more lights configured to illuminate based on one or more commands sent from the microcontroller.

3. The medical imaging patient bed as recited in claim 2, wherein the microcontroller is further configured to illuminate a plurality of the one or more lights corresponding to a range of distance measurements received from the laser distance meter.

4. The medical imaging patient bed as recited in claim 1, wherein the laser distance meter further comprises:
    a laser source configured to emit an emitted laser; and
    a laser receiver configured to receive a reflected laser;
    wherein the time between the emission of the emitted laser and the reception of the reflected laser determines the distance measurement.

5. The medical imaging patient bed as recited in claim 1, wherein the laser distance meter further comprises:
    a laser source configured to emit an emitted laser; and
    a laser receiver configured to receive a reflected laser;
    wherein the triangulation of the emitted laser and the reflected laser determines the distance measurement.

6. The medical imaging patient bed as recited in claim 1, wherein the trough and the light strip each have a length substantially similar to the length of the medical imaging patient bed.

7. The medical imaging patient bed as recited in claim 1, wherein the microcontroller is further configured to communicate the one or more distance measurements to an imaging system host controller.

8. The medical imaging patient bed as recited in claim 7, wherein the imaging system host controller is configured to adjust one or more parameters of a medical imaging scan based upon the one or more distance measurements received from the microcontroller.

9. The medical imaging patient bed as recited in claim 7, wherein the imaging system host controller is configured to use the one or more distance measurements for at least one of: creating one or more virtual switches, detecting one or more swipe gestures, adjusting one or more ranges, and detecting one or more imaging scan limits.

10. The medical imaging patient bed as recited in claim 1, wherein the microcontroller is further configured to extinguish the light strip and reset the laser distance meter after receiving a reset command.

11. The medical imaging patient bed as recited in claim 1, the closed end of the trough further comprising a reflective portion;
    wherein the distance meter is configured to be calibrated based on a distance measurement taken from the reflective portion of the trough.

12. An electronic ruler system, comprising:
    a light strip;
    a trough comprising an open end and a closed end;
    a distance meter attached to the open end of the trough; and
    a microcontroller;
    wherein the light strip is oriented such that the light strip is bounded by the open end and the closed end of the trough;
    wherein the microcontroller is configured to illuminate the light strip after one or more distance measurements are received from the distance meter when an object is inserted into the trough;
    wherein a position of the illumination of the light strip corresponds to the one or more distance measurements received from the distance meter.

13. The electronic ruler system as recited in claim 12, wherein the light strip further comprises one or more lights, the one or more lights configured to illuminate based on one or more commands sent from the microcontroller.

14. The electronic ruler system as recited in claim 13, wherein the microcontroller is further configured to illuminate a plurality of the one or more lights corresponding to a range of distance measurements received from the distance meter.

15. The electronic ruler system as recited in claim 12, wherein the distance meter comprises at least one of a laser distance meter, an ultrasound distance meter, or an infrared distance meter.

16. The electronic ruler system as recited in claim 15, wherein the at least one of the laser distance meter, ultrasound distance meter, or the infrared distance meter determines the one or more distance measurements through a time-of-flight determination.

17. The electronic ruler system as recited in claim 15, wherein the laser distance meter determines the one or more distance measurements through an optical triangulation.

18. The electronic ruler system as recited in claim 12, wherein the trough and the light strip are attached to a patient bed;
the trough and the light strip each having a length substantially similar to the length of the patient bed.

19. The electronic ruler system as recited in claim 12, wherein the microcontroller is further configured to communicate the one or more distance measurements to a host controller.

20. The electronic ruler system as recited in claim 19, wherein the host controller is configured to use the one or more distance measurements for at least one of: creating one or more virtual switches, detecting one or more swipe gestures, adjusting one or more ranges, and detecting one or more imaging scan limits.

21. The electronic ruler system as recited in claim 12, wherein the microcontroller is further configured to extinguish the light strip and reset the distance meter after receiving a reset command.

22. The electronic ruler system as recited in claim 12, the closed end of the trough further comprising a reflective portion;
wherein the distance meter is configured to be calibrated based on a distance measurement taken from the reflective portion of the trough.

23. A method of using an electronic ruler system, comprising:
generating, by a laser distance meter, an emitted laser;
receiving, by the laser distance meter, a reflected laser caused by the reflection of the emitted laser onto an object;
generating, by the laser distance meter, based upon properties of the emitted laser and the reflected laser, one or more distance measurements;
communicating, to a microcontroller, the one or more distance measurements; and
illuminating, by the microcontroller, a light strip in a manner corresponding to the one or more distance measurements received from the laser distance meter.

24. The method as recited in claim 23, further comprising:
communicating, by the microcontroller, the one or more distance measurements to a host controller; and
adjusting, by the host controller, one or more parameters of a medical imaging session based upon the one or more distance measurements.

* * * * *